United States Patent [19]

DelliColli et al.

[11] 4,244,729
[45] Jan. 13, 1981

[54] SUSTAINED RELEASE PESTICIDE COMPOSITIONS AND PROCESS FOR MAKING SAME

[75] Inventors: Humbert T. DelliColli; Peter Dilling, both of Charleston, S.C.

[73] Assignee: Westvaco Corporation, New York, N.Y.

[21] Appl. No.: 693,876

[22] Filed: Jun. 8, 1976

Related U.S. Application Data

[62] Division of Ser. No. 581,634, May 28, 1975, Pat. No. 4,184,866.

[51] Int. Cl.³ .............................................. A01N 25/04
[52] U.S. Cl. ........................................................ 71/65
[58] Field of Search ...................... 71/79, 65, DIG. 1; 424/19, 22; 260/124 A, 124 R

[56] References Cited

U.S. PATENT DOCUMENTS

| | | | |
|---|---|---|---|
| 3,470,148 | 9/1969 | Allan | 260/124 |
| 3,699,091 | 10/1972 | Dimitri et al. | 260/124 R |
| 3,718,639 | 2/1973 | Falkehag et al. | 260/124 A |
| 3,726,850 | 4/1973 | Detroit | 71/DIG. 1 |
| 3,865,803 | 2/1975 | Falkehag | 260/124 A |
| 3,886,101 | 5/1975 | Felicetta et al. | 260/124 A |
| 3,905,926 | 9/1975 | D'Alelio | 260/124 A |

*Primary Examiner*—Glennon H. Hollrah
*Attorney, Agent, or Firm*—Richard L. Schmalz; Ernest B. Lipscomb, III; Terry B. McDaniel

[57] ABSTRACT

A sustained release composition is disclosed which provides an improved carrier for an organic pesticide. The improved carrier is a reversibly swellable lignin gel made by cross-linking an alkali lignin with epichlorohydrin using particular conditions.

2 Claims, No Drawings

SUSTAINED RELEASE PESTICIDE COMPOSITIONS AND PROCESS FOR MAKING SAME

This is division of application Ser. No. 581,634, filed May 28, 1975, now U.S. Pat. No. 4,184,866

BACKGROUND OF THE INVENTION

1. Field of the Invention

This invention relates to sustained release pesticide compositions and processes for making the compositions. More particularly, this invention relates to an improved lignin-based carrier for the controlled release of organic water-insoluble pesticides or water-soluble salts of pesticides.

Technically, advantages to controlled release of pesticides are many and varied. The incorporation of a toxicant into a matrix offers protection to the pesticide from the degrading processes normally taking place. This makes possible the use of compounds less stable than halogenated hydrocarbons (e.g., carbamates, organophosphates, pyrethroids). Secondly, new uses for existing pesticides can be found. For example, Parathion and its derivatives cannot, because of degradation, be used in the soil unless very frequent applications at high dosage levels of material can be tolerated. Shelf life stability of formulations may also be increased for the above-mentioned reasons. In many underdeveloped parts of the world, pesticides are often applied by hand by individuals possessing little or no protective equipment. The slowed release of the toxicant results in a reduced toxicity to the persons working with it. Specialty applicants of pest control materials are realized through adoption of controlled release. An example can be found in animal feed throughs where a rapid and pin point release of a biologically active substance is desired.

2. Prior Art

As presently known, pesticides often have short useful lives; because they are degraded by bacteria to biologically inactive metabolites, or leached by rain into the subsoil where they are inaccessible to the pest they intend to control, or rendered inactive by voltilization, or by ultraviolet catalyzed degradation from exposure to sunlight. It is, therefore, desirable to provide a system whereby proper amounts of a biologically active organic pesticide may be continually released over a relatively long period of time. An up-to-date discussion of controlled release of pesticides and the desirability of using controlled release systems were present by Allan et al. in an article entitled "Pesticides, Pollution and Polymers" *Chem Tech* (March 1973).

Methods of obtaining controlled release or sustained release of pesticides are numerous in the prior art. U.S. Pat. No. 3,516,941 to G. W. Matson, for example, describes a method for obtaining controlled release of droplet size materials through microencapsulation.

U.S. Pat. No. 3,393,990 to R. J. Geary describes a pesticide composition wherein the pesticide is ground to a large surface area to exhibit its greatest effectiveness. The pesticide is held in place with a stabilized interpolymer substrate while it is slowly released.

U.S. Pat. No. 3,172,752 to H. L. Pierce is directed to a composition for the controlled release of an active agricultural substance. The composition is an enlarged particle formed from ground, expanded perlite which is properly sized and with hardened, slowly dissolving holding material of a viscous character before hardening. At least one active agricultural substance is uniformly dispersed therethrough and held to the particle covering the surfaces and filling the pores to intimately and tightly bind the agricultural substance to the perlite particles.

Another method for controlling the release of pesticides is provided in U.S. Pat. No. 3,813,236 to G. G. Allan. The Allan patent discloses chemical co-valent bonding of a pesticide to a lignin polymeric substrate. The pesticide is released by destruction of co-valent chemical bonds.

This invention, on the other hand, produces sustained release compositions by physically mixing pesticides with an improved carrier comprising a cross-linked reswellable lignin gel. It is, therefore, the general object of this invention to provide a sustained release composition having a pesticide interspersed and physically bound throughout a cross-linked reswellable alkali lignin gel.

Another object of this invention is to provide processes for interspersing a pesticide throughout an alkali lignin gel via physical contact forming a composite.

It is a specific object of this invention to provide a controlled release pesticide system comprising as a composite, a pesticide interspersed throughout an epichlorohydrin alkali lignin matrix whereby the release rate of the pesticide is accomplished through diffusion of the active ingredient through the alkali lignin matrix or through degradation or dissolution of the lignin matrix or a combination of both.

It is still another object of this invention to provide lignin composites containing pesticides which are stabilized against the degrading effects of sunlight.

It is an even further object of this invention to provide pesticide-containing composites which have controlled release that are substantially uneffected by rain.

It is yet another object of this invention to provide lignin matrixes containing pesticides which resist the action of micro-organisms.

Still another object of this invention is to provide controlled release pesticidal systems which maintain maximum and effective activity over prolonged periods of time under normal plant environmental conditions.

Other objects, features and advantages of this invention will become evident on reading the foregoing detailed description.

SUMMARY OF THE INVENTION

The uniqueness of alkali lignin as carrier for controlled release systems is supported by several facts. Perhaps, the most attractive property of alkali lignin is its chemical uniqueness. The functionality of the lignin phenolic hydroxyl, carboxylate, aliphatic hydroxyl groups, as well as, the higher aromatic content of the branch work comprising the lignin unit or molecule allows it to be modified. For example, blocking certain groups on the lignin unit or cross-linking the molecule can produce a three-dimensional matrix. Cross-linking can block polar functional groups or form C-C bonds between positions adjacent to the phenolic hydroxyls creating networks varying in pore structure and polarity. Once modified, the lignin can take the form of fine powders or coarse granules. Here the changes are purely physical and largely controlled by factors, such as drying conditions and means of grinding or milling.

The high aromatic content of lignin makes it an excellent ultraviolet radiation absorber. This is particularly important since many of the non-persistent pesticide and insect growth regulators in use are very sensitive to UV catalyzed hydrolysis or degradation. Such a process generally renders the pesticide biologically inactive. The antioxidant properties of lignin add further stability to materials incorporated into a lignin matrix. Lignin is a good dispersant, a desirable property for use in virtually all dry pesticide formulations, such as wettable powders, dusts or granules. The controlled release composites are converted to these conventional formulations. If some of the dispersant properties are already built into the matrix material, the preparation of conventional formulations is thus facilitated.

Although it is known to form controlled release systems based on alkali or kraft lignins, it is the subject of this invention to provide an improved lignin matrix for this purpose in which a carrier is formed by cross-linking lignin molecules with epichlorohydrin in such a manner as to form a reversible gel. For the purpose of this invention, a lignin gel shall mean a three-dimensional cross-linked matrix which can be repeatedly dehydrated and swollen to its original hydrated or swollen volume. The weight ratio of pesticide-to-lignin carrier is from 0.01:1.0 to 2:1.

DETAILED DESCRIPTION OF THE INVENTION

It has been found that improved controlled release properties may be obtained from the physical incorporation of a pesticide into a lignin gel by utilizing the improved lignin carrier of this invention.

Any of the alkali lignins may be employed to make the carrier used in this invention. These lignins are derived by the alkaline digestion of lignocellulosic material. Most commonly, they are obtained as byproducts from the alkaline process of paper making where sodium hydroxide alone or in combination with sodium sulfide is employed. These lignins are generally referred to as soda and kraft or sulfate lignins after the pulping process used. Such alkali lignin starting material is employed in the salt form, i.e., where the sodium or potassium cation has replaced the hydrogen, so it will be water soluble. Additionally, other water-solubilizing, salt-forming cations may be used, such as ammonia. In the preferred practice of this invention, the alkali lignin employed is a kraft pine lignin. Although sulfite waste liquor lignins and sulfonated alkali lignins may be used; they are not normally used because additional processing problems are involved.

The improved carrier is a gel which by I.U.P.A.C. definition means that it is reversibly swellable. The carrier is made by reacting a salt of a lignin which has been dissolved in a solution of from 10% to 25% (weight volume) of the lignin into water. It is also preferable that the pH be adjusted to between pH 11 and 12. To this solution is added epichlorohydrin in an amount of 1 to 10 moles of epichlorohydrin per 1,000 grams of lignin. The solution is heated to a temperature between 50° C. to 100° C., preferably 80° C. to 95° C., to perform the cross-linking reaction. The reaction is typically complete after about 2 hours but may be as short as 5 minutes. The material thus treated forms a reswellable lignin gel.

To assist in obtaining and preserving pore structures upon drying, the carrier gels may be prepared in the presence of barrier-type compounds or fillers. Exemplary fillers include sodium bicarbonate and sulfomethylated black liquor. When the filler materials are used, the gels after being produced are washed to remove any unreacted starting materials and unincorporated fillers. A protracted alkali wash may be followed by neutral water wash to remove the incorporated filler and leave the pores in the matrix. In the case of gels prepared using sodium bicarbonate, a dilute acid wash followed by the water wash also removes all traces of bicarbonate from the interstitial voids of the gels. The filler material may be used in an amount up to 50% by weight of the lignin material, preferably 5% to 30%. Typically speaking, the more porous the cross-linked lignin matrix gel the quicker the reversible swelling will take place.

The differing surface chemical characteristics of the gels make them attractive as controlled release carriers for different pesticides. The low dry surface area and almost non-existent anhydrous pore structure of the bicarbonate gel (e.g., say 1.8 m.$^2$/gm.) enables the carrier to accept and hold large quantities of liquid pesticides without rapid release of the toxicant. When the gel is dried, the loss of both area and apparent pore volume entraps much of the pesticide in the interior of the particles of the crosslinked lignin. Rapid release of the entrapped material does not take place because of the restricted diffusion of the pesticide through the carrier matrix whose apparent density has increased because of pore closure.

The higher surface area gels (e.g., 35 M.$^2$/gm.) are preferably used with solid pesticides and low melting point waxey solids. Excessive premature release of the liquid toxicant was observed with higher surface area gels at levels of loading greater than about 20% with some liquids. Conversely, attempts to load high concentrations of solid agents into the lower surface area gels produce composites with most of the pesticide on the surface of the particle. Such a system provides little control over the release of the toxicant or provides little protection to the material not immediately needed for biological control. The large pores remaining after the higher surface area gel is dried provide more accessibility of the pesticide to the environment than the lower surface area gel. This is necessary because of the slower movement of the solids from the carrier to the region adjacent to the particles or granules.

One particularly attractive feature of these gel carriers is the ability to exchange the water in the gels trapped during synthesis with methanol, ethanol, formamide, and other polar organic solvents. This makes it possible to load or impregnate the pores or voids of the gel with the pesticide with little or no water solubility.

The epichlorohydrin cross-linked gel carriers can be impregnated or "loaded" with pesticide in two ways. First and quite obviously, the easiest procedure is to simply slurry the dry carrier in a solution of the pesticide and evaporate the solvent. This results in a composite whose active material is held primarily on the surface of the carrier particles. Some diffusion of the toxicant into the interior of the carrier does take place if the pesticide is sufficiently polar. Since the greatest concentration of agent is at the surface, the loading of non-swollen gel is intended for the preparation of composites containing relatively low concentrations of pesticide. Composites prepared in this manner will probably have a short lifetime and would offer minimal protection to the agent from degradation.

Secondly, a preswollen "solvent exchanged" gel can be utilized. The carrier is preswollen in an alkaline solution, the pH lowered to neutral or slightly acidic pH values ($5 \leq pH \leq 7$), and the gel washed with methanol or any other appropriate solvent. The gel is then slurried in a solution of pesticide and the solvent evaporated. Composites prepared this way may be loaded with 35% by weight liquid pesticide and 50% by weight solids pesticide, i.e., 2 to 1 ratio, with no apparent loss of pesticide in subsequent crushing and screening operations. However, to be effective without using excessive amounts of carrier usually at least 0.01 to 1 pesticide-to-carrier is used. The specific details of carrier preparation and pesticide inclusion are described in the Examples.

The pesticides that can be physically combined with the cross-linked lignin materials described hereinabove primarily include those that are water-insoluble. Water-soluble salts of compounds can also be included in the carrier systems of this invention, but the control over the release of these pesticides is not as great because of their water-solubility. The water-soluble salts of pesticides will be released rapidly and over a shorter period of time than the water-insoluble pesticides. Some of the specific pesticides that may be employed include:

| Common Name | Proprietary Name | Chemical Description |
|---|---|---|
| Water-Insoluble Compounds | | |
| 2,4-D | — | 2,4-dichlorophenoxyacetic acid |
| dicamba | BANVEL | 3,6-dichloro-0-anisic acid |
| chlorpyrifos | DURSBAN | 0,0-diethyl 0-(3,5,6-trichloro-2-pyridyl-phosphorothioate |
| ethoprop | MOCAP | 0-ethyl S,S-dipropyl phosphorodithioate |
| leptophos | PHOSVEL | 0-(4-bromo-2,5-dichlorophenyl) 0-methyl-phenylphosphonothioate |
| methyl parathion | — | 0,0-dimethyl-0-p-nitrophenl) phosphorothioate |
| ethyl parathion | PARA-THION | 0,0,diethyl 0-P-nitrophenyl phosphorothioate |
| metalkamate | BUX | mixture of m-(ethylpropyl) phenyl methyl carbamate and m-(1-methyl butyl)phenyl methylcarbamate |
| carbofuran | FURADAN | 2,3-dihydro-2,2-dimethyl-7-benzofuranyl methyl carbamate |
| methoprene | ALTOSID | isopropyl 11-methoxy-3,7,11-trimethyldodeca-2,4-dienoate |
| — | ALTOZAR | ethyl 3,7,11-trimethyldodeca-2,4-dienoate |
| alachlor | LASSO | 2-chloro-2-'-6'-diethyl-N-(methoxymethyl)-acetanilide |
| diallate | AVADEX | 5-2,3-dichloroellyl diisopropylthio-carbamate |
| triallate | AVADEX BW | 2,2-dimethyl-3,5-diphenyl-1 H-pyrazolium methyl sulfate |
| bifenox | MODOWN | methyl 5-(2',4'-dichlorophenoxy)-2-nitrobenzoate |
| Water-Soluble Compounds | | |
| 2,4-D | — | 2,4-dichlorophenoxyacetic acid (amine or alkali salts) |
| dicamba | BANVEL | 3,6-dichloro-0-anisic acid |
| chloromben | AMIBEN | 3-amino-2,5-dichlorobenzoic acid (amine salt) |

The composite formulations consisting of carrier and pesticide can be prepared by a variety of techniques. The most straight forward is to slurry the solid carrier either swollen or non-swollen, in liquid pesticides, applying heat and allowing the system to cool. Excess pesticide is removed by decantation or filtration.

The pesticide may also be dissolved in the solvent used to remove water from the carrier. For example, the pesticide can be dissolved in either methanol, formamide, or dimethyl formamide. The carrier swollen in the same solvent is then slurried in the solution, and the solvent is evaporated. If high levels of pesticide loading are desired, (>25%) with solid pesticides, such as Dursban or Bux, the composite after excess solvent has been evaporated is first heated to the boiling point of the solvent and held at that temperature to remove the solvent. The temperature is then brought to the melting point of the pesticide and held there until the pesticide is melted. This system is then cooled rapidly to force excess pesticide into the interior of the carrier.

Another method is to dissolve the pesticide in a non-swelling solvent such as dichloromethane. The non-swollen carrier is heated, added to the solution, and the solvent evaporated. Heat may also be applied as above for solid agents. Composites may also be prepared using technology currently in use for preparing conventional granular formulations which utilize clay or ground corn cob for carrier. That is, the heated carrier can be sprayed with a solution of the agent in a volatile solvent, such as dichloromethane.

While composite formulations in the past have been prepared using chemically unmodified kraft lignin, certain advantages are realized with gel carriers of this invention which are not available with the unmodified lignins. For example, high levels of toxicant loading with kraft lignin frequently result in composites which have been sufficiently plasticized to prevent grinding and milling to granular and powder formulations. The specific interactions between carrier and pesticide which cause plasticization do not occur in the lignin gels of this invention. Secondly, use of unmodified lignin requires dissolution of the lignin in either organic solvents or concentrated aqueous alkali. This requires additional processing by the pesticide handling operator and in the case of alkaline solutions produces an environment into which few organophosphate or carbamate-type pesticides can be introduced. Use of aqueous lignin solutions produces effluents often contaminated with toxicant. The gels already consist of preformed 3-dimensional matrixes which after the initial preparation require no additional synthetic effort to produce a matrix.

Release of varying amounts of active pesticide can be controlled by the ratio of pesticide to lignin carrier. The amount of pesticide that is physically interspersed within the lignin gel is one of the factors which dictate the time which is needed for release of the pesticidal compound to the applicable site. The particular amount of cross-linking or processing conditions to form the lignin gels affects the release mechanism by virtue of the pore structure and cross-link density of the lignin gel. Thus, the amount of pesticide that is released over a given period of time can be controlled by selecting the process conditions for obtaining the cross-linked gels and the degree of loading of toxicant.

The sustained release compositions of this invention have numerous advantages to the ultimate user over other known pesticide compositions, these advantages including ease and handling solids as opposed to liquids, reduced toxicity to humans and other animal life, control of continuous release of active pesticide composites, lower risks of overapplication, and fewer and more efficient applications. The exact dosage applied depends upon the release rate of the composition, vegetation or insect to be controlled, the duration of control desired, and the pesticide employed.

The practice of this invention is clearly illustrated by the following examples.

EXAMPLE 1

This example illustrates the general procedure for modifying the lignin into the improved carrier. A sufficient amount of the sodium salt of kraft lignin was dissolved in water to make a solution of 20% weight by volume of the lignin and the pH was adjusted with sodium hydroxide to pH 11.5. A filler, sodium carbonate in an amount of 10% by weight of lignin was added to the solution and the temperature was brought to 85°–87° C. with stirring. To this solution was added 3 moles of epichlorohydrin per 1,000 grams of lignin over a 5-minute period while continuously stirring. The reaction was complete after 2 hours. The material thus treated formed a reswellable lignin gel and was stored wet with its own supernatant.

EXAMPLE 2

This example illustrates the importance of temperature in preparing the lignin gel carriers. Carriers were prepared from the lignin solutions and the procedures of Example 1 except that the carriers were cross-linked using various reaction temperatures.

| Sample | Temperature, °C. | Hours | Gel Formed |
|---|---|---|---|
| 1 | 23–27 | 12 | No |
| 2 | 45–50 | 8–10 | No |
| 3 | 70–75 | 6–8 | No |
| 4 | 85–87 | 2 | Yes |
| 5 | 90–95 | <1 | Yes |
| 6 | 100 | 0.085 | No |

Sample 1 after 12 hours reacting time formed a continuous system resembling pudding. Sample 3 at 70° C. formed discrete particles dispersed in a continuous medium of sufficient yield value for suspension of the particles was observed to form. Sample 6 run at 100° C. for about 5 minutes (0.085 hours) produced hard glassy nodules. None of the cross-linked lignins represented by samples 1–3 and 6 had the ability to be reswollen after initial dehydration; even after protracted heating in strongly alkaline solutions. Because they are not reswellable, they are not gels for the purpose of this invention. When thus treated and redried, samples 1 and 3 formed hard, brittle solids whose dry volume was less than 25% of that of the swollen sample. Also, these lignins when dried fractured spontaneously revealing highly reflective surfaces along the fracture lines. This indicates very close packing of the particles in the samples which consisted of suspended particles when swollen. The results show that in order to obtain a reswellable cross-linked gel carrier for the controlled release of water-soluble pesticides that the carrier must be made at a temperature bettween about 80° C. and 95° C.

EXAMPLE 3

This example illustrates the importance of adding the epichlorohydrin over a short period of time. Samples of the 20% lignin solution from Example 1 were heated to 80° C.–85° C. and 3 moles of epichlorohydrin were added with stirring over various periods of time.

| Sample No. | Time | Type of Gel |
|---|---|---|
| 1 | All at once | No gel |
| 2 | 2-3 minutes | Particulate reswellable gel |
| 3 | 10 minutes | Particulate gel |
| 4 | 15–20 minutes | Thin gellatinous fluid |
| 5 | 1–2 hours | Thin gellatinous fluid |
| 6 | 2 hours (4–5 parts) | Firm continuous gel |

As the results show, the desired gel is obtained when the epichlorohydrin is added over a relatively short period of time. If the epichlorohydrin is added dropwise over a prolonged period of time, i.e., sample 5, a thin gel with very little yield value is formed. This gel consists of particles in a continuous matrix and requires dehydration before it is sufficiently firm to resist flowing on its own. If the epichlorohydrin is added, i.e., sample 6, in four to five discrete aliquots over a 2-hour period, a firm continuous gel with about 40% reswellability results. Addition of the epichlorohydrin, i.e., sample 1, in one massive dose frequently results in the formation of a solid non-reswellable block of cross-linked lignin in the reaction vessel.

EXAMPLE 4

This example illustrates the critical nature of the starting lignin concentration. The general procedure of Example 1 was followed except that the starting concentration of lignin solution was varied.

| Sample No. | Lignin Concentration, % W/V | Reswellability |
|---|---|---|
| 1 | 5 | No |
| 2 | 10 | Marginal |
| 3 | 15 | Yes |
| 4 | 20 | Yes |
| 5 | 25 | Marginal |
| 6 | 50 | No |

The best results show that the lignin concentration should be between 15% and 20% weight by volume. Higher lignin concentrations have resulted in the formation of solids with little or no reswellability and porosity. Use of a lower concentration produces little product and requires additional reaction time for material to form.

EXAMPLE 5

This example illustrates the use of different lignin starting materials for making the reswellable lignin gel carrier using the conditions of Example 1.

| Sample No. | Starting Material | Reswellable Gel |
|---|---|---|
| 1 | Kraft Pine Lignin of Ex. 1 | Yes |
| 2 | Sodium salt of sulfonated kraft lignin | Yes |
| 3 | Sulfite Waste Liquor Lignin | Yes |

Both the sulfonated kraft lignin and the sulfite waste liquor lignin produced reswellable gels suitable as carriers for pesticides.

EXAMPLE 6

This example illustrates the effective on the carrier of different amounts of epichlorohydrin cross-linking using the general procedure of Example 1.

| Sample No. | Amount Epi. | Reaction Time | Gel |
|---|---|---|---|
| 1 | 1 mole | 15 minutes | poor |
| 2 | 1 mole | 2 hours | poor |
| 3 | 2 moles | 30 minutes | fair |
| 4 | 2 moles | 2 hours | good |
| 5 | 3 moles | 15 minutes | good |
| 6 | 3 moles | 2 hours | excellent |
| 7 | 5 moles | 5 minutes | poor |

The results indicate that the best gels were made by cross-linking the lignin with 3 moles of epichlorohydrin per 1,000 grams of lignin for 2 hours.

EXAMPLE 7

Once the carrier has been prepared it is readied for composite preparation by a series of washes. The first is with several volumes of water to remove unreacted lignin, inorganic salts and filler materials. This is followed by a wash with dilute acid to etch and remove the entrapped filler, when $NaHCO_3$ is used, and to neutralize residual base trapped in the gel. The trapped NaOH will, in a very short time, hydrolyze organophosphate and carbamate-type toxicants. The acid wash is then generally followed with an additional water wash to bring the pH of the system back to the 6–8 range and to remove any additional salts produced during the neutralization of entrapped base. These salts lower the pesticide holding capacity of the carrier by producing surfaces whose polarity is sufficiently high to reduce the adsorption of organic pesticides by the lignin. In the cases where the pesticide is soluble in the lignin, the presence of high inorganic salt concentrations reduces this solubility.

Further treatment of the carrier is not necessary when water-soluble pesticides, such as the salts of the phenoxyacetic acid-type herbicides, are used. Such materials, however, do not constitute the majority of the materials used in the current controlled release work; water-insoluble materials do. In such cases, water trapped in gel pores prevents penetration by the pesticide. Therefore, after the final water wash, the gel is freed of as much water as possible by filtration when it is to be used with a water-insoluble pesticide. When dried, the cross-linked lignin gel was a fine, free-flowing, red-brown powder with a surface area of 1.8 $M^2/gm$. ($N_2$ adsorption, B E T) and virtually no pore structure or a tan, sandy granular with a surface area of 35 $M^2/gm$. and well defined porosity. Carriers treated according to this Example 7 were made into controlled release composites in the following examples.

EXAMPLE 8

Dry gel was slurried in aqueous NaOH, pH=12, and heated to 75° C. for 2 hours. The supernatant was removed by filtration and the swollen gel washed with water until the pH of the effluent was equal to 8. The gel was reslurried in HCl, pH=3, for 15 minutes, filtered, and washed with 70° C. water until the pH of the effluent was neutral. The filter cake was then saturated with methanol, and the excess alcohol removed by filtration. This gel was found to contain 63.8% volatiles (36.2% solids content).

Two hundred-seventy and five-tenths grams (270.5 g.) of wet gel, 97.6 grams dry, were slurried in 1,000 ml. technical $CH_3OH$ and heated to 50° C. Fifty-six and eight-tenths grams (56.8 g.) ethoprop technical (Mocap), 92% active, were added to the methanol gel slurry. The slurry was brought to the boiling point of methanol and the alcohol allowed to evaporate. The result was 149.9 grams of a coarse reddish-brown granular composite.

EXAMPLE 9

One hundred-eighty grams (180 g.) dry non-swollen gel was heated in an oven to 115° C. and added to a solution of 21.82 grams of methoprene (Altosid), 92.4% active, in hexane. The hexane was allowed to evaporate at room temperature. The result was 200 grams of free-flowing red-brown powder.

EXAMPLE 10

A gel was reswollen as in Example 8 and was found to contain 32.9% solids. Three hundred thirty-two and one-tenth grams (332.1 g.) wet gel (112.5 grams dry carrier) was slurried in technical methanol in which 37.5 grams technical FMC 18739 (88.6% active) was dissolved. The result was 145 grams of soft red powder which was free flowing but which had the ability to adhere to smooth waxey surfaces.

EXAMPLE 11

Three hundred eighty-seven grams (387 g.) of wet swollen gel (22% solids) were slurried in 300 ml. technical methanol. Fifty-seven and two-tenths grams (57.2 g.) Bux technical (38.9 g. active) were dissolved in 200 ml. methanol and added to the gel slurry. The system was heated to 65° C. until all of the excess methanol was evaporated. The composite formulation which had a consistency of thick paste was then oven dried at a temperature of 40° C. The result was 140 grams of light tan granular material.

EXAMPLE 12

Five hundred fifteen grams (515 g.) of wet swollen gel (35% solids)=180 grams dry material were slurried in 500 ml. $H_2O$. Twenty-seven and nine-tenths milliliters (27.9 ml.) Amiben Super 6 which contained 20 grams amine salt of chloramben was added to the gel slurry. The pH of the slurry was adjusted to 3.5–4 with $H_2SO_4$ and the water evaporated. The result was 200 grams of reddish-brown powder.

EXAMPLE 13

In order to test the effectiveness of a lignin gel/ethoprop (Mocap) controlled release composite, three identical 1/50 acre plots were selected. One plot was treated with Mocap 10 G, a conventional granular formulation, at a rate of 5 lbs. active per acre; the second received no treatment and was referred to as the control. The third plot was treated with a 25% active lignin gel based controlled release composite (invention) at a rate of 4.0 lbs. of active per acre. The target specie was the root knot nematode of cucumber. The table below shows the results of the test.

| Treatment | Method of Application | Rate/Acre | Yield Per Acre | Root Knot Index |
|---|---|---|---|---|
| Control | | 0 | 210 | 3.0 |
| Ethoprop | Broadcast | 5 | 180 | 2.8 |
| Invention | Broadcast | 4 | 210 | 1.6 |

Root Knot Index = 0.0 (no root damage) - 5.0 (mass galls, decayed roots, etc.)

The controlled release composite provided better nematode control than its commercial counterpart with 20% less toxicant. A slight increase in yield per acre (not statistically significant) was observed. This is due to an apparent reduction in the phytotoxicity of the nematodecide and/or better nematode control.

While the invention has been described and illustrated herein by references to various specific materials, procedures and examples, it is understood that the invention is not restricted to the particular material, combinations of material, and procedures selected for that purpose. Numerous variations of such details can be implied as will be appreciated by those skilled in the art.

What is claimed is:

1. In a process for making a controlled release pesticide carrier, the improvement comprising,
    (a) reacting alkali lignin solution at a concentration of between 10% and 25% by volume with from 1 to 5 moles of epichlorohydrin at a temperature between about 50° C. and 100° C. for from 5 minutes to 2 hours to thereby form a reversibly swellable gel.
2. The process of claim 1 wherein up to 50% of a barrier material from the group consisting of sodium bicarbonate and sulfomethylated black liquor is added during the reaction, and washed out after the gel is formed.

UNITED STATES PATENT AND TRADEMARK OFFICE
CERTIFICATE OF CORRECTION

PATENT NO. : 4,244,729

DATED : January 13, 1981

INVENTOR(S) : Humbert T. DelliColli, Peter Dilling and Sten I. Falkehag

It is certified that error appears in the above—identified patent and that said Letters Patent is hereby corrected as shown below:

In column 1 of the Title Page, line 6 stating the Inventors, after "both of Charleston, S. C.", insert --Sten I. Falkehag, Mt. Pleasant, S. C.--.

In column 1, line 6, after the word "is" and before the word "division", insert --a--.

In column 1, line 43, "voltilization," should read --volatilization,--.

In column 1, line 67, after the word "and" and before the word "with", insert --dried. The expanded perlite particles are coated and impregnated--.

In column 5, under the heading Water-Insoluble Compounds, line 32, "0,0-dimethyl-0-p-nitrophenl)" should read --0,0-dimethyl-0-P-nitrophenyl--; line 44, "5-2,3-dichloroellyl diisopropylthio-" should read --5-2,3-dichloroallyl diisopropylthio--; and line 46, "2,2-dimethyl-3,5-diphenyl-1 H-" should read --1,2-dimethyl-3,5-diphenyl-1 H---.

UNITED STATES PATENT AND TRADEMARK OFFICE
CERTIFICATE OF CORRECTION

PATENT NO. : 4,244,729

DATED : January 13, 1981

INVENTOR(S) : Humbert T. DelliColli, Peter Dilling and Sten I. Falkehag

It is certified that error appears in the above—identified patent and that said Letters Patent is hereby corrected as shown below:

In column 5, under the heading Water-Soluble Compounds, line 53, "chloromben" should read --chloramben--.

In column 7, Example 2, line 55, "bettween" should read --between--.

In column 8, Example 6, line 66, "effective" should read --effect--.

Signed and Sealed this

Ninth Day of February 1982

[SEAL]

Attest:

Attesting Officer

GERALD J. MOSSINGHOFF

Commissioner of Patents and Trademarks